United States Patent
Shin et al.

(10) Patent No.: US 10,502,647 B2
(45) Date of Patent: Dec. 10, 2019

(54) APPARATUS FOR MEASURING UNDERWATER PRESSURE

(71) Applicant: KOREA INSTITUTE OF OCEAN SCIENCE & TECHNOLOGY, Gyeonggi-do (KR)

(72) Inventors: Chang Joo Shin, Gyeonggi-do (KR); Jung Min Seo, Gyeonggi-do (KR); O Soon Kwon, Gyeonggi-do (KR); Won Dae Baek, Gyeonggi-do (KR)

(73) Assignee: Korea Institute of Ocean Science & Technology, Gyeonggi-do (KR)

( * ) Notice: Subject to any disclaimer, the term of this patent is extended or adjusted under 35 U.S.C. 154(b) by 179 days.

(21) Appl. No.: 15/740,464

(22) PCT Filed: Feb. 14, 2017

(86) PCT No.: PCT/KR2017/001594
§ 371 (c)(1),
(2) Date: Dec. 28, 2017

(87) PCT Pub. No.: WO2018/151338
PCT Pub. Date: Aug. 23, 2018

(65) Prior Publication Data
US 2018/0372569 A1    Dec. 27, 2018

(51) Int. Cl.
*G01L 7/04*     (2006.01)
*G01L 19/06*    (2006.01)
*G01L 19/00*    (2006.01)
*G01N 1/16*     (2006.01)

(52) U.S. Cl.
CPC ............ *G01L 7/04* (2013.01); *G01L 19/0023* (2013.01); *G01L 19/06* (2013.01); *G01L 19/0636* (2013.01); *G01N 1/16* (2013.01)

(58) Field of Classification Search
CPC .. G01D 5/22; G21C 17/06; G01L 7/04; G01L 19/06; G01L 19/0636
See application file for complete search history.

(56) References Cited

U.S. PATENT DOCUMENTS 6,467,331 B1 * 10/2002 Kline-Schoder ......... A61B 8/08
239/9
8,130,986 B2 *  3/2012 White .................. H04R 19/005
381/165

FOREIGN PATENT DOCUMENTS

KR          101158413 B1    6/2012

* cited by examiner

*Primary Examiner* — Harshad R Patel
*Assistant Examiner* — Nigel H Plumb
(74) *Attorney, Agent, or Firm* — RatnerPrestia

(57) ABSTRACT

According to the present disclosure, at least two fluid inlet/outlet pipes, each of which is provided with a filter, are installed outside a structure to be bent and an end of each of the fluid inlet/outlet pipes is connected to a pressure sensor provided on the structure. Thus, since a fluid in the state in which low-frequency and high-frequency components of the disturbances generated outside the structure are removed therefrom acts on the pressure sensor, the underwater pressure sensing apparatus is capable of measuring fluid pressure in a stable state.

10 Claims, 4 Drawing Sheets

APPARATUS FOR MEASURING UNDERWATER PRESSURE

CROSS REFERENCE TO RELATED APPLICATIONS

This application is the U.S. National Phase Application of PCT/KR2017/001594, filed Feb. 14, 2017, the contents of such application being incorporated by reference herein.

TECHNICAL FIELD

The present disclosure relates to an apparatus for measuring an underwater pressure. More particularly, the present disclosure relates to an underwater pressure measurement apparatus, in which two or more fluid inlet/outlet pipes communicating with a pressure sensor are provided outside a structure (or a housing) in which the pressure sensor is accommodated and a filter is provided at an end of each pipe such that a high-frequency disturbances component generated in the water outside the housing are removed by the filter and a low-frequency component of the disturbances is removed while passing through the fluid inlet/outlet pipes, whereby the underwater pressure measurement apparatus is capable of measuring a quasi-static pressure in the state in which low-frequency and high-frequency components are removed.

BACKGROUND ART

In order to measure the depth of water, a pressure gauge is generally used. Such a pressure gauge is attached to the outer surface of a structure (including underwater moving body), and receives pressure, which is received by the structure, at the same time, thereby measuring the underwater pressure.

However, when disturbances (vortexes or strong tidal currents generated by the operation of a thruster) are applied to the structure, the water pressure becomes relatively low or high, and as a result the measured depth of water may differ from the actual depth of water at which the equipment exists. That is, there is a problem in that since the accurate water pressure cannot be measured due to the disturbances, the accurate depth of water cannot be determined.

As a prior art, Korean Patent No. 10-1158413 (published on Jun. 22, 2012) discloses a radiation-resistant Linear Variable Differential Transform (LVDT) for pressure measurement. The radiation-resistant LVDT for pressure measurement is adapted to measure pressure under a high-temperature and high-pressure condition. However, since there is not provided means for removing the low-frequency and high-frequency of disturbances that are generated from the outside of the structure, it is difficult to perform stable pressure measurement.

DETAILED DESCRIPTION OF THE INVENTION

Technical Problem

An aspect of the present disclosure is to provide a mechanism capable of measuring underwater pressure stably and accurately without being affected by strong tidal currents or vortexes or the like, which are caused by the operation of a thruster, by enabling a quasi-static pressure in the state in which low-frequency and high-frequency components of various disturbances occurring in the water outside a structure (a structured article or a housing) are removed, to be measured by a pressure sensor within the structure.

Technical Solution

According to the present disclosure, an underwater pressure measurement apparatus includes: a structure having a configuration in which an interior and an exterior are separated from each other such that inflow of a fluid is blocked; a pressure sensor configured to measure pressure of the fluid and installed inside the structure; and two or more fluid inlet/outlet pipes, each formed in a hollow shape such that the fluid flows into or flows out of the two or more fluid inlet/outlet pipes, each of which is connected, at one end thereof, to the pressure sensor and is provided, at a remaining end, with a filter configured to block inflow of foreign matter and to remove a high-frequency component of disturbances, the two or more fluid inlet/outlet pipes being made of a bendable material and being disposed outside the structure. When the fluid flowing into the fluid inlet/outlet pipes through the filter acts on the pressure sensor, a high-frequency component and a low-frequency component of the disturbances generated in water are removed while passing through the filter and the fluid inlet/outlet pipes.

The structure may include a cover member configured to open/close the interior thereof, and the pressure sensor may be installed on the cover member so that a portion of the pressure sensor is located outside the cover member, and the one end of each of the fluid inlet/outlet pipes may be connected to the pressure sensor exposed to the exterior such that the fluid, which flows into and out of the fluid inlet/outlet pipes acts on the pressure sensor.

The filter may be made of at least one material selected from a group consisting of a mesh body, porous sponge, fabric, a porous synthetic resin body, and a porous fiber.

The filter may include a hollow first connector that is provided and replaceably coupled to the remaining end of each of the fluid inlet/outlet pipes, and a hollow second connector configured to be connected to the first connector by being fastened or fitted to the first connector and coupled to the filter.

The cover member may include a plurality of fixing members configured to fix positions and a bent state of the fluid inlet/outlet pipes and the filter, and each of the fixing members may include a coupling end fastened or fitted to the cover member and a fixing end with a fitting groove configured to fit each of the fluid inlet/outlet pipes or the filter therein.

Each of the fluid inlet/outlet pipes may have a low-frequency removing section which is formed by being bent in a curved shape or at a right angle such that the low frequency is removed as the fluid interferes with the low-frequency removing section while flowing into/out of the fluid inlet/outlet pipes.

Advantageous Effects

According to the present disclosure, at least two fluid inlet/outlet pipes, each of which is provided with a filter, are installed outside a structure to be bent and an end of each of the fluid inlet/outlet pipes is connected to a pressure sensor provided on the structure. Thus, since a fluid in the state in which low-frequency and high-frequency components of the disturbances generated under water outside the structure are removed therefrom acts on the pressure sensor, the underwater pressure sensing apparatus is capable of measuring fluid pressure in a stable state.

In addition, the filter installed at the remaining end of each of the fluid inlet/outlet pipes not only can remove the high frequency of the disturbances, but also can prevent the foreign matter in the water from flowing into the fluid inlet/outlet pipes.

In addition, since the filter is replaceably provided at the remaining end of each of the fluid inlet/outlet pipe, it is possible to provide an effect that the filter can be easily replaced or cleaned.

Further, since each of the fluid inlet/outlet pipes is freely bent and disposed on the cover member of the structure, it is possible to diversify the configuration of the structure or to couple various structures to the cover member. That is, the shape of the structure can provide an effect that enables the configuration to be variously designed.

DESCRIPTIONS OF REFERENCE NUMERALS OF MAIN PARTS IN DRAWINGS

10: underwater pressure measurement apparatus, 20: structure, 22: cover member, 30: pressure sensor, 32: case, 40: filter, 42: first connector, 44: second connector, 50, 50A, 50B: fluid inlet/outlet pipe, 52: low frequency removing section, 60: fixing member, 62: coupling end, 64: fixing end, 64: fitting groove;

MODE FOR CARRYING OUT THE INVENTION

The underwater pressure measurement apparatus of the present disclosure includes a structure configured to measure pressure under water and having a configuration in which an interior and an exterior are separated so as to block inflow of a fluid. The underwater pressure measurement apparatus includes a pressure sensor configured to measure the pressure of a fluid and installed inside the structure. The underwater pressure measurement apparatus includes two or more fluid inlet/outlet pipes, each formed in a hollow shape such that the fluid flows into or flows out of the two or more fluid inlet/outlet pipes, each of which is connected, at one end thereof, to the pressure sensor and is provided, at a remaining end, with a filter configured to remove a high-frequency component of disturbances, the two or more fluid inlet/outlet pipes being made of a bendable material and being disposed outside the structure. When the fluid flowing into the fluid inlet/outlet pipes through the filter acts on the pressure sensor, a high-frequency component and a low-frequency component of the disturbances generated in water are removed while passing through the filter and the fluid inlet/outlet pipes, so that the pressure sensor can measure a quasi-static pressure.

Hereinafter, embodiments of the present disclosure will be described in detail with reference to the accompanying drawings. However, in the following description of the present disclosure, descriptions of well-known functions or constructions will be omitted in order to make the gist of the present disclosure clear.

Figure 1:
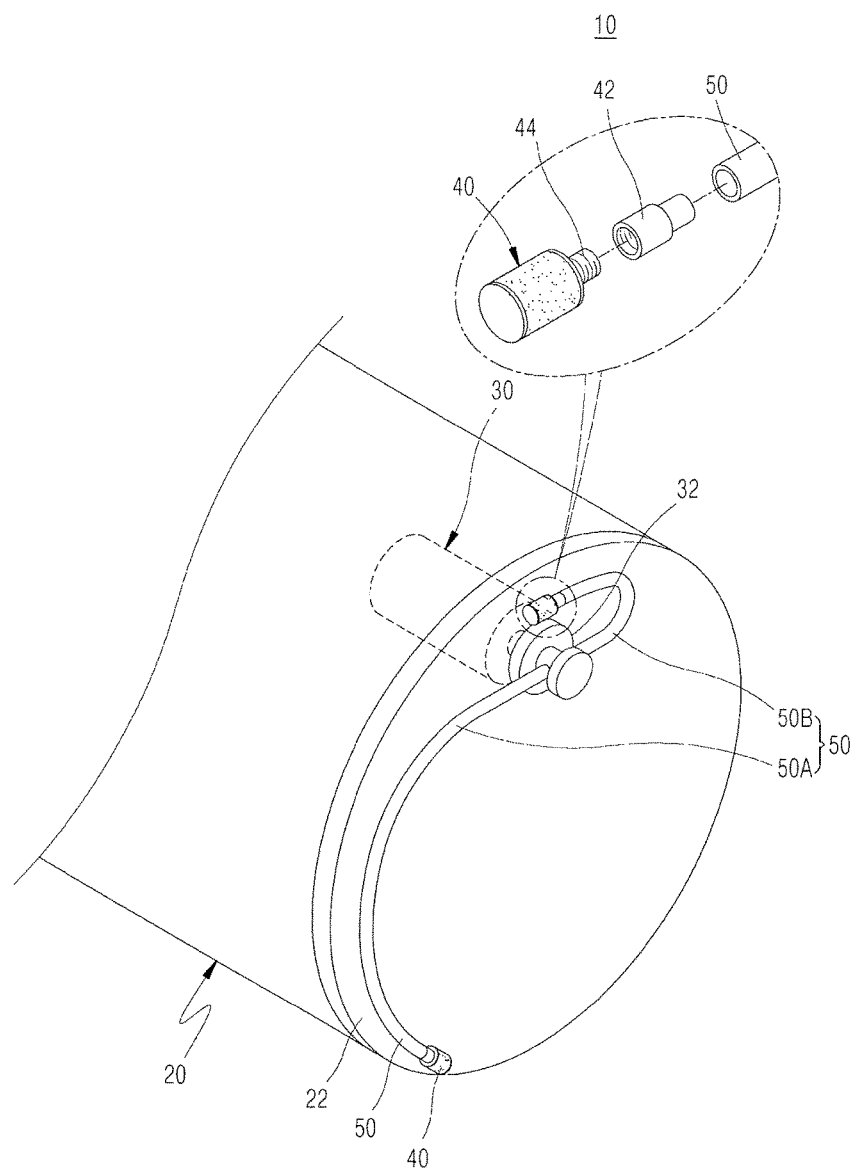
FIG. 1 is a perspective view illustrating an underwater pressure measurement apparatus according to the present disclosure.
Figure 2:
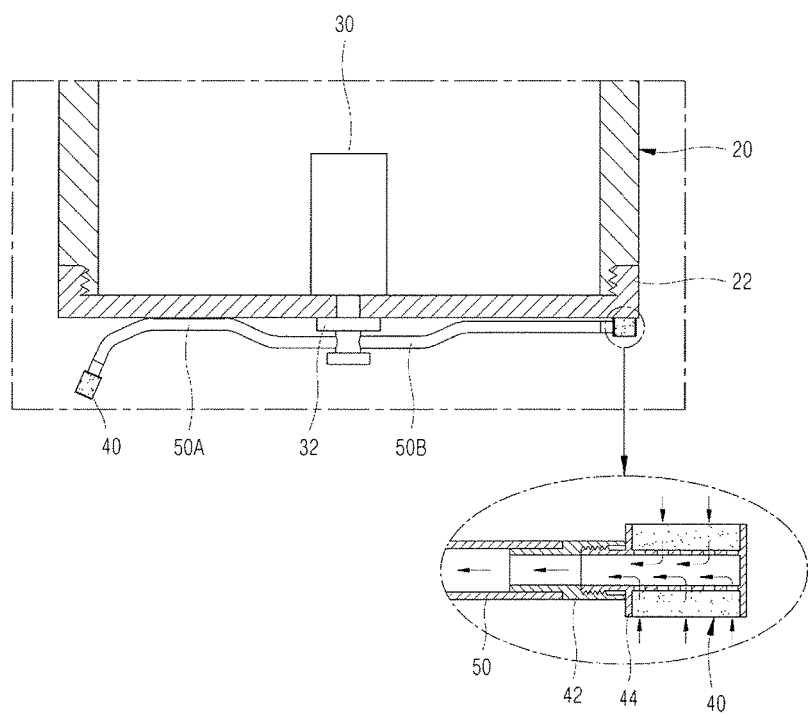
FIG. 2 is a schematic sectional view showing the underwater pressure measurement apparatus illustrated in FIG. 1.
Figure 3:
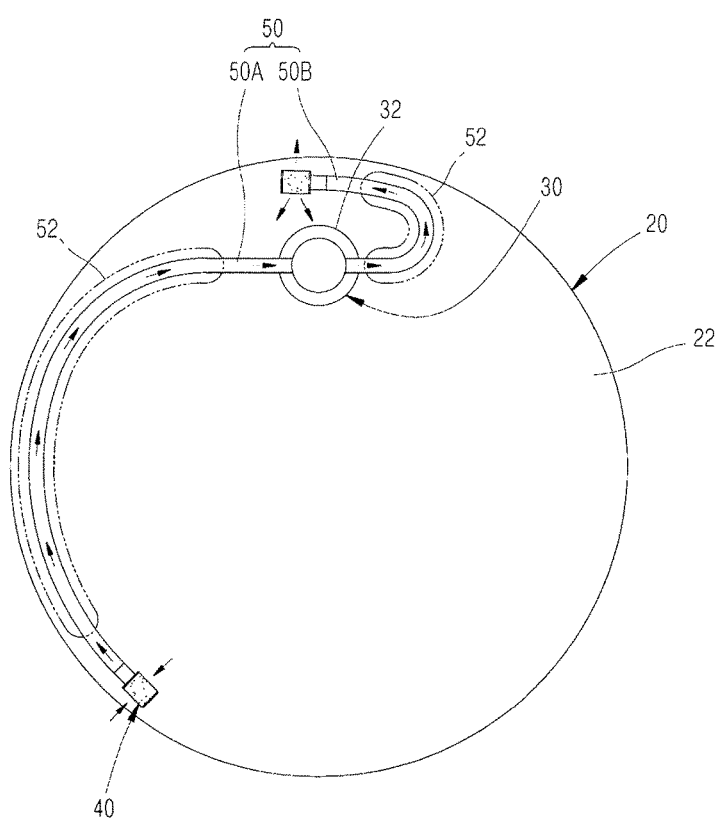
FIG. 3 is a front view illustrating the underwater pressure measurement apparatus illustrated in FIG. 1.

FIG. 1 is a perspective view illustrating an underwater pressure measurement apparatus according to the present disclosure, FIG. 2 is a schematic sectional view showing the underwater pressure measurement apparatus illustrated in FIG. 1, FIG. 3 is a front view illustrating the underwater pressure measurement apparatus illustrated in FIG. 1.

As illustrated in FIGS. 1 to 3, an underwater pressure measurement apparatus 10 according to the present disclosure is for measuring underwater pressure, and includes a structure (20) having a configuration in which the exterior and the interior are separated so as to block the inflow of the fluid, a pressure sensor 30 configured to measure a fluid pressure and installed inside the structure 20, and two or more fluid inlet/outlet pipes 50, each of which is formed in a hollow shape such that fluid flows thereinto or flows out therefrom and has one end connected to a pressure sensor 30 and a remaining end provided with a filter 40 configured to block the inflow of foreign matter. The two or more fluid inlet/outlet pipes 50 are made of a flexible material and are disposed outside the structure 20.

This will be described in more detail.

The structure 20 includes a cover member 22 configured to open and close the inside thereof. In the structure 20, the inside and outside are separated from each other by the cover member 22 such that the fluid does not flow into the inside.

Figure 4:
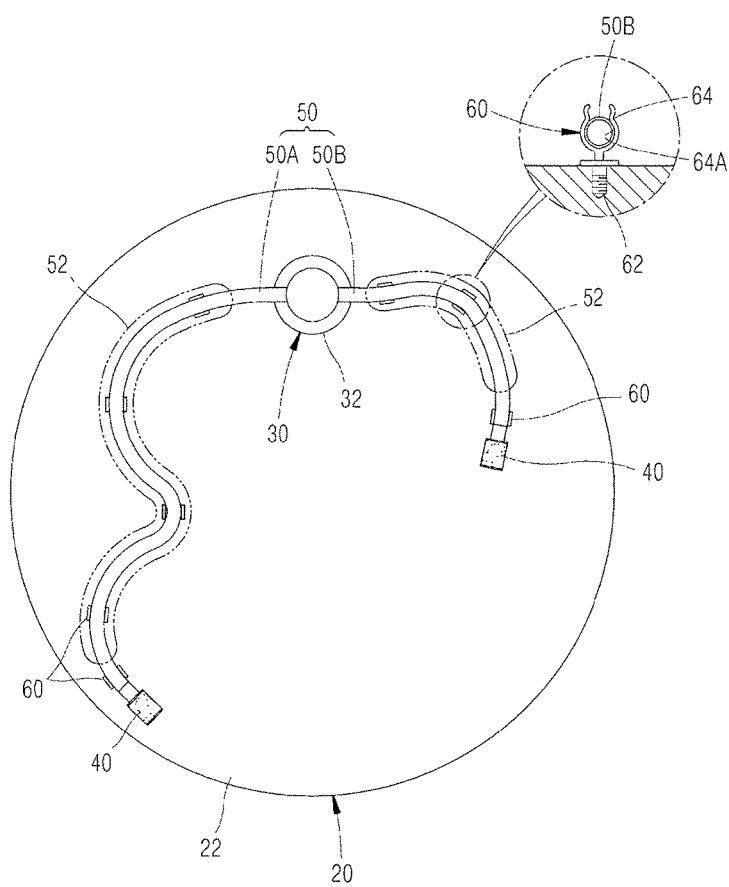
FIG. 4 is a front view illustrating another embodiment of the underwater pressure measurement apparatus illustrated in FIG. 1.

As illustrated in FIG. 4, the cover member 22 is provided with a plurality of fixing members 60 configured to fix the positions and bent states of the fluid inlet/outlet pipes 50 and the filters 40 and to prevent the movements of the fluid inlet/outlet pipes 50 and the filters 40.

Each fixing member 60 includes a coupling end 62 which is fastened to the cover member 22. A pair of fixing ends 64 are formed to upwardly protrude from the coupling end 62 so as to form a fitting groove 64A configured to fit the fluid inlet/outlet pipe 50 or the filter 40 thereinto. That is, a coupling end 62 to be fastened to the cover member 22 is formed on one end of the fixing member 60, and two fixing ends 64 are formed on the other end to be spaced apart from each other such that the fitting groove 64A is formed therebetween. Accordingly, the position of the fluid inlet/outlet pipe 50 can be fixed by fitting the fluid inlet/outlet pipe 50 into the fitting groove 64A.

The pressure sensor 30 is installed on the cover member 22 so as to be positioned inside the structure 20, and has a configuration in which a sensing unit (not illustrated) is provided inside a case 32. The pressure sensor 30 is installed on the cover member 22 such that a part of the pressure sensor 30 is located outside the cover member 22. In addition, one end of each fluid inlet/outlet pipe 50 is coupled to a part of the pressure sensor 30 that is exposed to the outside of the structure 20. That is, one end of each fluid inlet/outlet pipe 50 is coupled to a part of the pressure sensor 30 such that the pressure of a fluid introduced through the fluid inlet/outlet pipe 50 acts on the pressure sensor 30. Here, since the pressure sensor 30 for measuring water pressure has a known configuration, a detailed description thereof will be omitted.

The fluid inlet/outlet pipe 50 serves to guide the fluid outside the structure 20 to reach the pressure sensor 30, and to remove a high frequency or low frequency generated in the fluid flowing into the pressure sensor 30. The fluid inlet/outlet pipe 50 is formed in a hollow shape so as to allow the fluid to flow into and to flow out from the fluid inlet/outlet pipe 50. One end of each fluid inlet/outlet pipe 50 is connected to the pressure sensor 30, and the other end of the fluid inlet/outlet pipe 50 is connected to a filter 40 configured to block inflow of foreign matter. There are provided two or more fluid inlet/outlet pipes 50, which are made of two or more flexible materials and disposed outside the structure 20.

Each fluid inlet/outlet pipe 50 may be made of a flexible material including a synthetic resin material, urethane, a rubber material, or the like, and may be formed of a metal pipe. In addition, the outer surfaces of the fluid inlet/outlet pipes 50 may be covered, clothed, or coated with a cover for buffering an impact transmitted from the outside. For example, by configuring a buffer member by forming a buffer layer with a urethane foam or by covering a cover made of a rubber material on the outer circumferential surface of the fluid inlet/outlet pipe 50, various external forces including disturbances generated in the water are prevented from acting on the fluid inlet/outlet pipe 50 itself such that the external forces do not affect the fluid passing through the fluid inlet/outlet pipe 50.

As illustrated in FIGS. 1, 3, and 4, at least one low frequency removing section 52, which is bent in a curved line shape, is formed in the fluid inlet/outlet pipe 50. This low frequency removing section 52 is for removing a low frequency component of disturbances generated outside the structure 20. For example, when a fluid flows into the fluid inlet/outlet pipes 50 through one fluid inlet/outlet pipe 50A and moves to the other fluid inlet/outlet pipe 50B, the low frequency component of the fluid is removed while passing through multi-bent low frequency sections 52. That is, since a low-frequency signal has a long wavelength, the low-frequency signal is removed while passing through the multi-bent low-frequency removing sections 52 that shape the fluid inlet/outlet pipes 50 in a long length.

The low frequency removing section 52 may be formed in various forms and may be formed at a plurality of places by the fixing member 60 as illustrated in FIG. 4.

Meanwhile, although the present embodiment provides two inlet/outlet pipes 50, the present disclosure is not limited thereto. At least two fluid inlet/outlet pipes may be provided, and three or more (e.g., three to ten) may be provided as needed. This configuration is provided due to the following reason. When any one fluid inlet/outlet pipe 50 is damaged by an external force or the filter 40 provided at the end of the fluid inlet/outlet pipe 50 is clogged by foreign matter or the like, the flow of fluid into/out of the fluid inlet/outlet pipe 50 is blocked. Thus, at least two fluid inlet/outlet pipes 50 are provided in order to ensure that when the flow of fluid into/out of any one fluid inlet/outlet pipe 50 is blocked, the other fluid inlet/outlet pipe 50 performs the role of the blocked fluid inlet/outlet pipe 50.

The filter 40 is coupled to the other end of each fluid inlet/outlet pipe 50 in order to filter foreign matter contained in the fluid that flows into the fluid inlet/outlet pipe 50. In addition, the filter 40 functions to prevent cavitation, high frequency, vortexes, etc. at the inlet of each fluid inlet/outlet pipe 50. That is, the fluid passes through fine pores formed in the filter 40 so that high frequency, vortexes, or the like including cavitation included in the fluid can be removed.

The filter 40 is made of at least one material selected from a group consisting of a mesh body, porous sponge, fabric, a porous synthetic resin body, and a porous fiber. Alternatively, the filter 40 may be configured with a porous sintered body in which solid particles having a grain size of 1 mm or less are sintered in a specific form so as to form fine pores between the solid particles.

Meanwhile, the filter 40 is removably coupled to the other end of each fluid inlet/outlet pipe 50 for easy replacement. That is, as illustrated in FIG. 3, the filter 40 is replaceably coupled to the other end of the fluid inlet/outlet pipe 50. For this purpose, the other end of the fluid inlet/outlet pipe 50 is provided with a hollow first connector 42 and a hollow second connector 44 connected to the first connector 42 by being fastened or fitted to the first connector 42 such that the second connector 44 is coupled to the filter 40. Engagement protrusions are formed on the outer circumferential surface of one end of the first connector 42 such that the first connector 42 is firmly engaged with the fluid inlet/outlet pipe 50. The fluid inlet/outlet pipe 50 may be tightened with a clamp in the state in which one end of the first connector 42 is inserted into the fluid inlet/outlet pipe 50 as necessary, so that the fluid inlet/outlet pipe 50 can be firmly coupled with the first connector 42. In this embodiment, a female screw thread is formed on the inner circumferential surface of the first connector 42, and a male screw thread is formed on the outer circumferential surface of one end of the second connector 44 such that the female and male screws are screwed together. On one end of the second connector 44, a male screw is formed and the other end of the second connector 44 has a structure to which the filter 40 is coupled.

Due to the coupling structure of the first connector 42 and the second connector 44, the operation of coupling/separating the filter 40 to/from the fluid inlet/outlet pipe 50 can be easily and quickly performed. In addition, the filter 40 can be easily cleaned by such a replacement structure.

The action of the underwater pressure measurement apparatus 10 configured as described above will be described.

The underwater pressure measurement apparatus 10 configured as described above is placed under water (or another fluid).

When the structure 20 is placed in underwater, the fluid passes through the filter 40 provided in the end of each of the fluid inlet/outlet pipes 50A and 50B and flows into the inside thereof. The fluid may flow into one fluid inlet/outlet pipe 50A, may act on the sensing unit of the pressure sensor 30, and may then be discharged through the other fluid inlet/outlet pipe 50B. Of course, the fluid may flow in the direction opposite the above-described flow direction.

Since the fluid flows into the fluid inlet/outlet pipe 50A and acts on the sensing unit of the pressure sensor 30, the pressure sensor 30 measures the pressure of the fluid.

In this way, the pressure sensor 30 is not exposed to the fluid outside the structure 20, and acts on the sensing unit only through the fluid inlet/outlet pipes 50A and 50B. Therefore, the pressure sensor 30 can measure the correct pressure in a stable state. That is, since the inside of the structure 20 does not come into direct contact with the fluid, the influence of disturbances generated outside the structure is minimized, and thus the sensing unit of the pressure sensor 30 is capable of measuring the fluid pressure in a relatively stable state.

Meanwhile, a high-frequency component by disturbances of various factors generated outside the structure 20 is removed by being interfered with the filters 40 when flowing into the inside of the fluid inlet/outlet pipes 50A and 50B through the filters 40, which are provided on the ends of the fluid inlet/outlet pipes 50A and 50B, respectively.

The fluid, from which the high frequency component is removed by the filter 40 while flowing into one fluid inlet/outlet pipe 50A through the above-described process, acts on the sensing unit of the pressure sensor 30, and then is discharged to the outside through the other fluid inlet/outlet pipe 50B. That is, the fluid outside the structure 20 passes through the flow path formed by both the fluid inlet/outlet pipes 50A and 50B. As described above, the fluid flowing (passing) through the flow path formed by the fluid inlet/outlet pipes 50A and 50B acts on the sensing unit of the pressure sensor 30 connected to one end of each of the fluid inlet/outlet pipes 50A and 50B.

As described above, the low frequency of the fluid flowing in the flow path (inside the fluid inlet/outlet pipes), which is formed by the fluid inlet/outlet pipes 50A and 50B, is removed while passing through the low frequency removing sections 52 bent at a right angle or in a circular or curved shape. That is, when the fluid flows into the fluid inlet/outlet pipes 50 through one fluid inlet/outlet pipe 50A and moves to the other fluid inlet/outlet pipe 50B after acting on the sensing unit of the pressure sensor 30, a low-frequency component having a long wavelength is removed while passing through the multi-bent low frequency removing sections 52. That is, since the low-frequency signal has a long wavelength, the low-frequency signal can be removed while passing through the multi-bent low frequency removing sections 52 that shape the fluid inlet/outlet pipes 50 in a long length.

As described above, the fluid, which has been affected by disturbances generated by various factors outside the structure 20, acts on the sensing unit of the pressure sensor 30 in a stable state in which a high-frequency component and a low frequency component are removed therefrom while passing through the filters 40 and the frequency removing sections 52 of the fluid inlet/outlet pipes 50, so that the pressure sensed by the sensing unit becomes a quasi-static pressure in the state in which high-frequency and low-frequency components are removed from disturbances.

Therefore, the pressure sensor 30 is capable of stably measuring fluid pressure under water in which disturbances including vortexes due to various factors occur.

Meanwhile, such an underwater pressure measurement apparatus 10 can be used for an underwater moving body, particularly a Remotely Operated Vehicle (ROV), and can be usefully used when a static pressure measurement is required at a position where flow velocity is high.

Although specific embodiments of the present disclosure have been described and illustrated above, it is evident to a person ordinarily skilled in the art that the present disclosure is not limited to the described embodiments, and various changes and modifications can be made without departing from the technical idea and scope of the present disclosure. Accordingly, such modifications or variations should not be understood individually from the technical spirit and viewpoint of the present disclosure, and the modifications and variations should be deemed to fall within the scope of the claims of the present disclosure.

INDUSTRIAL APPLICABILITY

The underwater pressure sensing apparatus according to the present disclosure is configured such that at least two fluid inlet/outlet pipes, each of which is provided with a filter, are installed outside a structure to be bent and an end of each of the fluid inlet/outlet pipes is connected to a pressure sensor provided on the structure. Thus, since a fluid in the state in which low-frequency and high-frequency components of disturbances generated outside the structure are removed therefrom acts on the pressure sensor, the underwater pressure sensing apparatus is capable of measuring fluid pressure in a stable state. Therefore, the underwater pressure measurement apparatus according to the present disclosure may be applied to a ship or an underwater moving body, in particular, an unmanned submarine, and may be usefully used when a static pressure measurement is required at a position where flow velocity is high. Further, it is obvious that the present disclosure can be practically carried out. Thus, the present disclosure is an industrially applicable invention.

The invention claimed is:

1. An underwater pressure measurement apparatus for measuring pressure under water, the apparatus comprising:
   a structure having a configuration in which an interior and an exterior are separated from each other such that inflow of a fluid is blocked;
   a pressure sensor configured to measure pressure of the fluid and installed inside the structure; and
   two or more fluid inlet/outlet pipes, each formed in a hollow shape such that the fluid flows into or flows out of the two or more fluid inlet/outlet pipes, each of which is connected, at one end thereof, to the pressure sensor and is provided, at a remaining end, with a filter configured to block inflow of foreign matter and to remove a high-frequency component of a disturbance, the two or more fluid inlet/outlet pipes being made of a bendable material and being disposed outside the structure, wherein when the fluid flowing into the fluid inlet/outlet pipes through the filter acts on the pressure sensor, a high-frequency component and a low-frequency component of the disturbance generated in water are removed while passing through the filter and the fluid inlet/outlet pipes.

2. The apparatus of claim 1, wherein the structure includes a cover member configured to open/close the interior thereof, and the pressure sensor is installed on the cover member so that a portion of the pressure sensor is located outside the cover member, and the one end of each of the fluid inlet/outlet pipes is connected to the pressure sensor exposed to the exterior such that the fluid, which flows into and out of the fluid inlet/outlet pipes acts on the pressure sensor.

3. The apparatus of claim 2, wherein the cover member includes a plurality of fixing members configured to fix positions and a bent state of the fluid inlet/outlet pipes and the filter, and each of the fixing members includes a coupling end fastened or fitted to the cover member and a fixing end with a fitting groove configured to fit each of the fluid inlet/outlet pipes or the filter therein.

4. The apparatus of claim 3, wherein each of the fluid inlet/outlet pipes has a low-frequency removing section which is formed by being bent in a curved shape or at a right angle such that the low frequency is removed as the fluid interferes with the low-frequency removing section while flowing into/out of the fluid inlet/outlet pipes.

5. The apparatus of claim 1, wherein each of the fluid inlet/outlet pipes has a low-frequency removing section which is formed by being bent in a curved shape or at a right angle such that the low frequency is removed as the fluid interferes with the low-frequency removing section while flowing into/out of the fluid inlet/outlet pipes.

6. The apparatus of claim 2, wherein each of the fluid inlet/outlet pipes has a low-frequency removing section which is formed by being bent in a curved shape or at a right angle such that the low frequency is removed as the fluid interferes with the low-frequency removing section while flowing into/out of the fluid inlet/outlet pipes.

7. The apparatus of claim 1, wherein the filter is made of at least one material selected from a group consisting of a mesh body, porous sponge, fabric, a porous synthetic resin body, and a porous fiber.

8. The apparatus of claim 7, wherein each of the fluid inlet/outlet pipes has a low-frequency removing section which is formed by being bent in a curved shape or at a right angle such that the low frequency is removed as the fluid interferes with the low-frequency removing section while flowing into/out of the fluid inlet/outlet pipes.

9. The apparatus of claim 1, wherein the filter includes a hollow first connector that is provided and replaceably coupled to the remaining end of each of the fluid inlet/outlet pipes; and a hollow second connector configured to be connected to the first connector by being fastened or fitted to the first connector and coupled to the filter.

10. The apparatus of claim 9, wherein each of the fluid inlet/outlet pipes has a low-frequency removing section which is formed by being bent in a curved shape or at a right angle such that the low frequency is removed as the fluid interferes with the low-frequency removing section while flowing into/out of the fluid inlet/outlet pipes.

\* \* \* \* \*